US009590438B2

(12) United States Patent
Dalton et al.

(10) Patent No.: US 9,590,438 B2
(45) Date of Patent: Mar. 7, 2017

(54) SYSTEMS, DEVICES, AND METHODS FOR CONTROL OF A POWER SUPPLY CONNECTION

(71) Applicant: ABBOTT DIABETES CARE INC., Alameda, CA (US)

(72) Inventors: Scott D. Dalton, Berkeley, CA (US); Theodore J. Kunich, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 187 days.

(21) Appl. No.: 14/529,833

(22) Filed: Oct. 31, 2014

(65) Prior Publication Data
US 2015/0123641 A1 May 7, 2015

Related U.S. Application Data

(60) Provisional application No. 61/899,983, filed on Nov. 5, 2013.

(51) Int. Cl.
*H02J 7/00* (2006.01)
*H03K 17/687* (2006.01)

(52) U.S. Cl.
CPC .................................. *H02J 7/0063* (2013.01)

(58) Field of Classification Search
CPC .................................................... H03K 17/687
USPC .......................................................... 307/140
See application file for complete search history.

(56) References Cited

U.S. PATENT DOCUMENTS

| | | |
|---|---|---|
| 5,465,400 A | 11/1995 | Norimatsu |
| 5,790,961 A | 8/1998 | Ingram et al. |
| 6,377,894 B1 | 4/2002 | Deweese et al. |
| 6,616,819 B1 | 9/2003 | Liamos et al. |
| 7,418,285 B2 | 8/2008 | Ghesquiere et al. |
| 7,749,740 B2 | 7/2010 | Eiteman et al. |
| 2004/0118704 A1 | 6/2004 | Wang et al. |
| 2006/0091006 A1 | 5/2006 | Wang et al. |
| 2006/0193375 A1 | 8/2006 | Lee |
| 2008/0066305 A1 | 3/2008 | Wang et al. |
| 2008/0267823 A1 | 10/2008 | Wang et al. |
| 2010/0094110 A1 | 4/2010 | Heller et al. |
| 2010/0094111 A1 | 4/2010 | Heller et al. |
| 2010/0094112 A1 | 4/2010 | Heller et al. |
| 2010/0198034 A1 | 8/2010 | Thomas et al. |
| 2010/0198142 A1 | 8/2010 | Sloan et al. |
| 2010/0265073 A1 | 10/2010 | Harper |
| 2010/0324392 A1 | 12/2010 | Yee et al. |
| 2011/0082484 A1 | 4/2011 | Saravia et al. |
| 2011/0106126 A1 | 5/2011 | Love et al. |
| 2011/0184264 A1 | 7/2011 | Galasso et al. |
| 2011/0190603 A1 | 8/2011 | Stafford |
| 2011/0191044 A1 | 8/2011 | Stafford |

(Continued)

FOREIGN PATENT DOCUMENTS

| | | |
|---|---|---|
| JP | 09-046900 | 2/1997 |
| WO | PCT/US2014/063442 | 2/2015 |
| WO | PCT/US2014/063442 | 5/2016 |

*Primary Examiner* — Robert Deberadinis
(74) *Attorney, Agent, or Firm* — One LLP

(57) ABSTRACT

A power supply control circuit for a portable electronic device is capable of connecting and disconnecting a power supply with respect to an electrical load of the device. The power supply control circuit offers a relatively quick transition time and low leakage current, making the control circuit particularly suitable for applications that require the power supply to remain connected to the electrical load at all times.

20 Claims, 7 Drawing Sheets

(56) References Cited

U.S. PATENT DOCUMENTS

| | | |
|---|---|---|
| 2011/0193704 A1 | 8/2011 | Harper et al. |
| 2011/0256024 A1 | 10/2011 | Cole et al. |
| 2011/0282175 A1 | 11/2011 | Geissler et al. |
| 2011/0319729 A1 | 12/2011 | Donnay et al. |
| 2012/0136610 A1 | 5/2012 | Fennell |
| 2012/0197222 A1 | 8/2012 | Donnay et al. |
| 2013/0241745 A1 | 9/2013 | Colvin, Jr. et al. |

SYSTEMS, DEVICES, AND METHODS FOR CONTROL OF A POWER SUPPLY CONNECTION

CROSS-REFERENCE TO RELATED APPLICATIONS

This application claims priority to and the benefit of U.S. Provisional Application Ser. No. 61/899,983, filed Nov. 5, 2013, which is incorporated by reference herein in its entirety for all purposes.

FIELD

The subject matter described herein relates to systems, devices, and methods for control of a power supply connection, for example, with respect to the connection and disconnection of a battery in a handheld device forming part of an in vivo analyte monitoring system.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Systems have been developed for the automatic monitoring of analyte(s), like glucose, in bodily fluid such as in the blood stream, in interstitial fluid ("ISF"), or in other biological fluid. Some of these analyte measuring systems are configured so that at least a portion of a sensor control device is positioned below a skin surface of a user, e.g., in a blood vessel or in the subcutaneous tissue of a user, so that the monitoring is accomplished in vivo. As such, these systems are typically referred to as "in vivo" monitoring systems. They are in contrast to "in vitro" systems that contact a sample outside the body (or rather "ex vivo") and typically include a meter device that has a port for receiving an analyte test strip carrying bodily fluid of the user, which can be analyzed to determine the user's blood sugar level.

In vivo analyte monitoring systems can be broadly classified based on the manner in which data is communicated between the reader device and the sensor control device. One type of in vivo system is a "Continuous Analyte Monitoring" system (or "Continuous Glucose Monitoring" system), where data can be broadcast from the sensor control device to the reader device continuously without prompting, e.g., in an automatic fashion according to a broadcast schedule. Another type of in vivo system is a "Flash Analyte Monitoring" system (or "Flash Glucose Monitoring" system or simply "Flash" system), where data can be transferred from the sensor control device in response to a scan or request for data by the reader device, such as with a Near Field Communication (NFC) or Radio Frequency Identification (RFID) protocol.

Both in vivo and in vitro systems typically contain a power supply and electronics for performing the blood sugar analyses. The systems are provided to the user through typical medical device distribution channels, and these channels can become filled with inventory, which could result in a device residing on the shelf for a lengthy duration of time between manufacture and first use. A concern exists that, during this time, any on-board power supply, such as a battery, might become drained of its current supplying capacity. This concern is exacerbated by the trend towards ever smaller and more power efficient devices, which use smaller and less powerful batteries.

In the past, battery leakage in a product residing on the shelf was minimized by the placement of an insulator between the battery and the physical electrical contact through which the battery supplies current. For example, a removable paper insulator was placed directly between the battery and the device's battery contact, such that a user could remove the insulator and thereby initiate electrical contact just prior to first use. However, this solution requires that the user has physical access to the battery, which may not be the case in a design where the battery is located wholly within the device housing in an inaccessible fashion. This solution also requires an additional step of user intervention prior to first use of the device, which can negatively impact the marketability of the device.

In other cases, the battery was placed in direct electrical contact with the leads of the device, but a control circuit was used to prevent the battery from connection to the electrical load of the on-board circuitry. Whenever the device was activated, the control circuit would form a closed path between the battery and the electrical load of the device to supply power. Whenever the device was deactivated, the control circuit would open the path between the battery and the electrical load so as to disconnect the battery and minimize any current leakage therefrom.

However, new applications have arisen, such as with respect to in vivo monitoring, where it has become desirable to leave the battery in a connected state at all times, even when the in vivo monitoring device is deactivated, or powered off. While such a device does not draw current to power its electrical circuitry in the deactivated state, the battery remains connected and the control circuit continues to draw power in the form of leakage current. Prior control circuits suffer from leakage levels that are too high to permit the battery to remain in a connected state when the monitoring device is deactivated.

Accordingly, needs exist for improved in vivo and in vitro analyte monitoring devices having increased shelf-life, greater power efficiency, greater flexibility to be used in new analyte monitoring applications, and greater control of performance.

SUMMARY

Analyte monitoring systems are provided having one or more portable devices containing one or more power supplies. Examples of the portable devices include, but are not limited to: an on-body electronics device with a sensor for in vivo monitoring of an analyte level of a subject; a display device (or reader, or reader device) for interfacing with the on-body electronics device and receiving data from the on-body electronics device that is indicative of the monitored analyte level of the subject and, optionally, processing the data and displaying the data to the subject or other user; and an in vitro analyte meter. In certain embodiments, the power supply is contained within a housing of the portable device such that the power supply is not replaceable by a user.

The power supply can be readily connected and disconnected from the electrical circuitry, or load, which that power supply is intended to source by way of a power supply control circuit. In many embodiments, the power supply control circuit can operate with low leakage currents, allowing the power supply to remain connected for long periods of time without losing significant current driving capability or efficiency. Also, in many embodiments the power supply control circuit can operate with a relatively fast response time, permitting its use with reader devices that require quick activation for reading data from other devices, such as through a near field communication (NFC) scan.

In certain embodiments, the control circuit has no path that exhibits only resistance between the power supply and a ground node, e.g., no path that includes only a wire, via, connector, or resistor (ignoring parasitic capacitance and/or inductance). In certain embodiments, the only paths between the power supply and a ground node within the control circuit pass through one or more transistors and/or capacitors.

In certain embodiments, the control circuit is transitionable from a disconnected state where one or more power supplies are electrically disconnected from an electrical load, to a connected state where the one or more power supplies are electrically connected to the electrical load. The control circuit can include an input node that receives a control signal, as well as a first transistor activatable to permit the supply of power from the power supply through the first transistor to the electrical load and deactivatable to prevent the supply of power from the power supply to the electrical load. The control circuit can also include a second transistor coupled with the input node and configured to activate a fourth transistor in response to a first voltage of the control signal. The control circuit can also include a third transistor coupled with the input node and configured to control the activation of the first transistor in response to a second voltage of the control signal.

In certain embodiments, each of the transistors is a field effect transistor (FET), where the first and second transistors are P-type and the third and fourth transistors are N-type. A source of the first transistor can be coupled with a source of the second transistor and a positive terminal of the power supply, and a drain of the first transistor can be coupled with the electrical load. A gate of the first transistor can be coupled with a drain of the third transistor, and a source of the third transistor can be coupled with a ground node. A gate of the second transistor can be coupled with the input node and a drain of the fourth transistor, a gate of the fourth transistor can be coupled with a drain of the second transistor and a drain of the third transistor, and a source of the fourth transistor can be coupled with the ground node. Further, a resistive feedback path can be present between the input node and the electrical load.

In certain embodiments, the control circuit can include a first capacitor coupled between a gate of the second transistor and the ground node, a second capacitor coupled between a positive terminal and a negative terminal of the power supply, and a third capacitor coupled between a drain of the first transistor and the ground node.

In certain embodiments, the control circuit can include a first resistor coupled between the gate of the second transistor and the drain of the fourth transistor, and a second resistor coupled between the drain of the second transistor and the gate of the fourth transistor.

Example embodiments of methods of connecting a power supply to an electrical load in a portable device are disclosed. In certain embodiments of these methods, the portable device has a control circuit with a first transistor electrically located between the power supply and the electrical load, a second transistor having a gate coupled to an input node, a third transistor having a gate coupled to the input node, and a fourth transistor. In some embodiments, the method includes activating the third transistor with a first voltage applied at the input node, activating the first transistor with a second voltage applied by the third transistor, where activation of the first transistor electrically connects the power supply to the electrical load, deactivating the fourth transistor with the second voltage, and deactivating the second transistor, where the second transistor is electrically located between the power supply and the fourth transistor.

In certain embodiments, the second transistor is deactivated by the first voltage applied at the input node. In some embodiments, a resistive feedback path is present between the electrical load and the input node, and a first capacitor is coupled between the input node and a ground node, and the method further includes applying a relatively high impedance to the input node. The second transistor can be deactivated after charging the first capacitor through the resistive feedback path.

Example embodiments of methods of disconnecting a power supply from an electrical load in a portable device are disclosed. In certain embodiments of these methods, the portable device has a first transistor electrically located between the power supply and the electrical load, a second transistor having a gate coupled to an input node, a third transistor having a gate coupled to the input node, and a fourth transistor. In some embodiments, the method includes deactivating the third transistor with a first voltage applied at the input node, activating the second transistor with the first voltage applied at the input node, deactivating the first transistor with a second voltage applied by the second transistor, where deactivation of the first transistor electrically disconnects the power supply from the electrical load, and activating the fourth transistor with the second voltage to maintain the deactivation of the third transistor.

In certain embodiments, a resistive feedback path is present between the electrical load and the input node, and a first capacitor is coupled between the input node and a ground node, and the method further includes applying a relatively high impedance to the input node.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
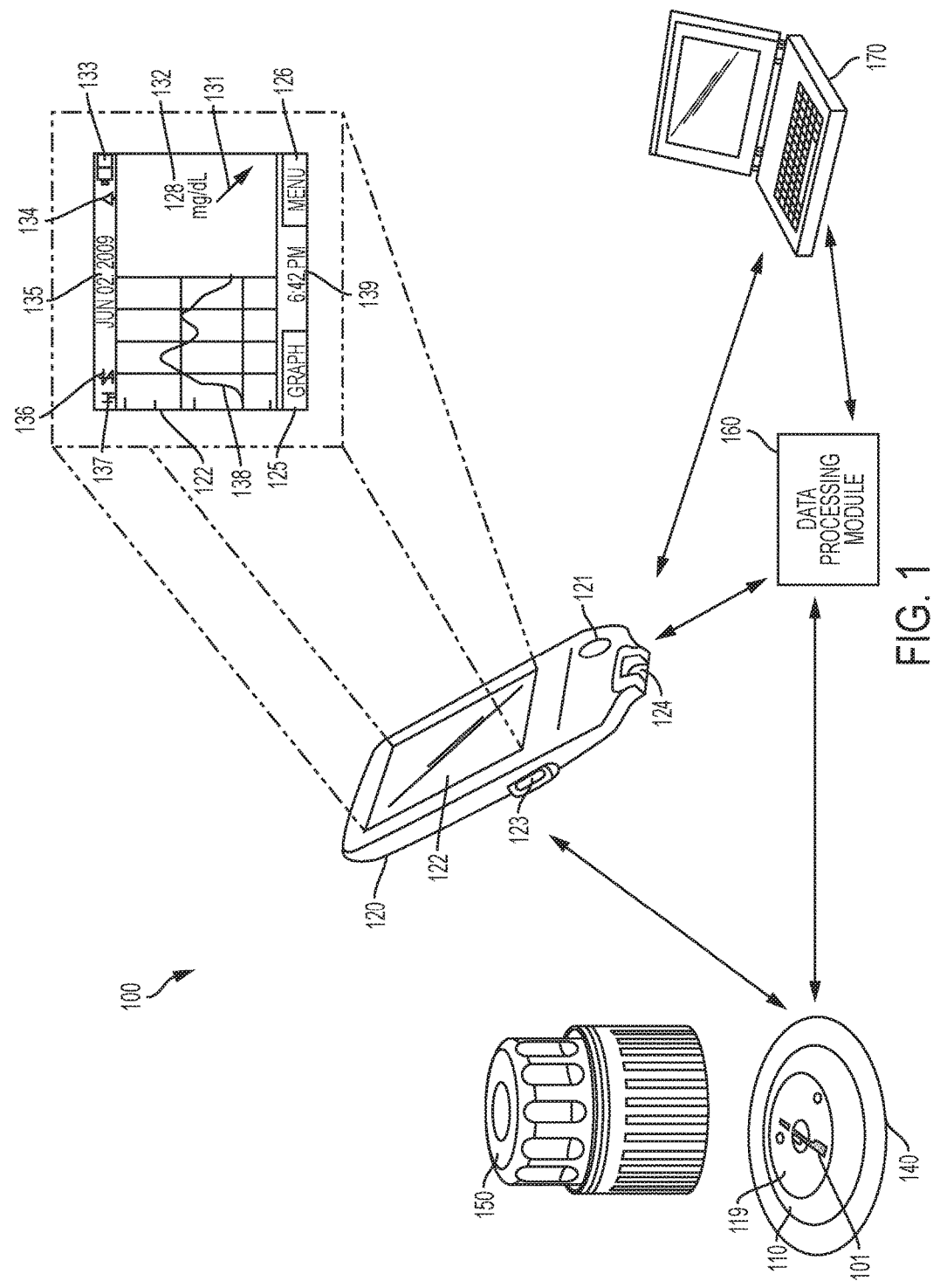
FIG. 1 is a high level diagram depicting example embodiments of an analyte monitoring system for real time analyte (e.g., glucose) measurement, data acquisition and/or processing.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is noted that each intervening value, to the tenth of the unit of the lower limit unless the context clearly dictates otherwise, between the upper and lower limit of that range and any other stated or intervening value in that stated range, is encompassed within the disclosure and can be claimed as an sole value or as a smaller range. Where the stated range includes one or both of the limits, ranges excluding either or both of those included limits are also included in the disclosure.

Where a discrete value or range of values is provided, it is noted that that value or range of values may be claimed more broadly than as a discrete number or range of numbers, unless indicated otherwise. For example, each value or range of values provided herein may be claimed as an approximation and this paragraph serves as antecedent basis and written support for the introduction of claims, at any time, that recite each such value or range of values as "approximately" that value, "approximately" that range of values, "about" that value, and/or "about" that range of values. Conversely, if a value or range of values is stated as an approximation or generalization, e.g., approximately X or about X, then that value or range of values can be claimed discretely without using such a broadening term.

However, in no way should a claim be limited to a particular value or range of values absent explicit recitation of that value or range of values in the claims. Values and ranges of values are provided herein merely as examples.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Generally, embodiments of the present disclosure relate to all types of in vivo (e.g., CGM, flash, etc.) and in vitro methods, systems, and devices for detecting and/or monitoring at least one analyte such as glucose in body fluid. Accordingly, some embodiments include in vivo analyte sensors configured so that at least a portion of the sensor is positioned in the body of a user (e.g., within the ISF), to obtain information about at least one analyte of the body, e.g., transcutaneously or subcutaneously positioned in user's body.

In certain embodiments, an in vivo analyte sensor is coupled to an electronics unit e.g., that is maintained on the body of the user, such as on a skin surface, where such coupling provides on-body, in vivo analyte sensor electronics assemblies.

In certain embodiments, analyte information is communicated from a first device such as an on-body electronics unit to a second device that may include user interface features, including a display, and/or the like. Information may be communicated from the first device to the second device automatically and/or continuously when the analyte information is available, or may not be communicated automatically and/or continuously, but rather stored or logged in a memory of the first device, e.g., for later output such as when retrieved by the second device when a user initiates a data retrieval. Accordingly, in many embodiments of the system, analyte information derived by the sensor/on-body electronics (for example, the on-body electronics device) is made available in a user-usable or viewable form only when queried by the user such that the timing of data communication is selected by the user.

In this manner, analyte information is only provided or evident to a user (provided at a user interface device) when desired by the user even though an in vivo analyte sensor may automatically and/or continuously monitor the analyte level in vivo, i.e., the sensor automatically monitors an analyte such as glucose on a pre-defined time interval over its usage life. For example, an analyte sensor may be positioned in vivo and coupled to on-body electronics for a given in vivo monitoring period, e.g., 7 days, 14 days, or longer, such as 30 days or more. In certain embodiments, the sensor-derived analyte information is automatically communicated from the sensor electronics assembly to a remote monitor device or display device for output to a user throughout the monitoring period (e.g., 14 day period) according to a schedule programmed at the on-body electronics (e.g., about every 1 minute, about every 5 minutes, about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated and sensor-derived information is then sent from the on-body electronics to the remote device or display device.

In still other embodiments, the information may be communicated from the first device to the second device automatically and/or continuously when the analyte information is available, but the second device stores or logs the received information without presenting or outputting the information to the user until, e.g., the user makes a request for the information. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device. In other words, the second device receives the information without a user request, but displays the information only after a user request (or a request from another device or person).

Accordingly, in certain embodiments once a sensor electronics assembly is placed on the body so that at least a portion of the in vivo sensor is in contact with bodily fluid such as ISF or dermal fluid and the sensor is electrically coupled to the electronics unit, sensor derived analyte information may be communicated from the on-body electronics to a display device on-demand by powering on the display device (or it may be continually powered), and executing a software algorithm stored in and accessed from a memory of the display device, to generate one or more requests, commands, control signals, or data packets to send to the on-body electronics. The software algorithm executed under, for example, the control of the microprocessor or application specific integrated circuit (ASIC) of the display device may include routines to detect the position of the on-body electronics relative to the display device to initiate the transmission of the generated requests, commands, control signals, and/or data packets.

Display devices may also include programming stored in memory for execution by one or more microprocessors and/or ASICs to generate and transmit the one or more requests, commands, control signals, or data packets to send to the on-body electronics in response to a user activation of an input mechanism on the display device such as depressing a button on the display device, triggering a soft button associated with the data communication function, and so on. The input mechanism may be alternatively or additionally provided on or in the on-body electronics, which may be configured for user activation. In certain embodiments, voice commands or audible signals may be used to prompt or instruct the microprocessor or ASIC to execute the software routine(s) stored in the memory to generate and transmit the one or more requests, commands, control signals, or data packets to the on-body electronics device. In the embodiments that are voice-activated or responsive to voice commands or audible signals, on-body electronics and/or the display device includes a microphone, a speaker, and processing routines stored in the respective memories of the on-body electronics and/or the display device to process the voice commands and/or audible signals. In certain embodiments, positioning the on-body electronics device and the display device within a predetermined distance (e.g., close proximity) relative to each other initiates one or more software routines stored in the memory of the display device to generate and transmit a request, command, control signal, or data packet.

Different types, forms, and/or amounts of information may be sent for each on-demand reading, including, but not limited to, one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), or historical analyte information corresponding to analyte information obtained prior to a given reading and stored in a memory of the assembly. Some or all of real time, historical, rate of change, rate of rate of change (such as acceleration or deceleration) information may be sent to a display device for a given reading. In certain embodiments, the type, form, and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on-body electronics (e.g., in the form of a graphical trace). Additionally, the on-skin or sensor temperature reading or measurement associated with each on demand reading may be communicated from the on-body electronics to the display device. The temperature reading or measurement, however, may not be output or displayed on the display device, but rather, used in conjunction with a software routine executed by the display device to correct or compensate the analyte measurement output to the user on the display device.

As described, embodiments include in vivo analyte sensors and on-body electronics that together provide body wearable sensor electronics assemblies. In certain embodiments, in vivo analyte sensors are fully integrated with on-body electronics (fixedly connected during manufacture), while in other embodiments they are separate but connectable post manufacture (e.g., before, during, or after sensor insertion into a body). On-body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on-body electronics assemblies completely in an interior compartment, i.e., an insertion device may be "pre-loaded" with on-body electronics assemblies during the manufacturing process (e.g., on-body electronics may be packaged in a sterile interior compartment of an insertion device). In such embodiments, insertion devices may form sensor assembly packages (including sterile packages) for pre-use or new on-body electronics assemblies, and insertion devices configured to apply on-body electronics assemblies to recipient bodies.

Some embodiments include portable handheld display devices, e.g., the above-referenced "second device," as separate devices and spaced apart from an on-body electronics assembly that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on-body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but not limited to stand-alone or network connection enabled data management software program, resident or running on a display device, personal computer, a server terminal, for example, to perform data analysis, charting, data storage, data archiving, and data communication as well as data synchronization. Informatics software in certain embodiments may also include software for executing field upgradable functions to upgrade firmware of a display device and/or on-body electronics unit to upgrade the resident software on the display device and/or the on-body electronics unit, e.g., with versions of firmware that include additional features and/or include software bugs or errors fixed, etc.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on-body electronics unit. Informatics programming may transform data acquired and stored on a display device or on-body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

For example, analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hemoglobin A1C, hormones, ketones, lactate, oxygen, peroxide, prostate-specific antigen, pro-thrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times, with a single sensor or with a plurality of sensors which may use the same on-body electronics (e.g., simultaneously) or with different on-body electronics.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be, e.g., less than about 1 hour, about 1 hour or more, about a few hours or more, about a few days of more, about 3 or more days, about 5 days or more, about 7 days or more, about 10 days or more, about 14 days or more, about several weeks, or about 1 month or more. In certain embodiments, after the expiration of the predetermined monitoring time period, one or more features of the system may be automatically deactivated or disabled at the on-body electronics assembly and/or display device.

For example, a predetermined monitoring time period may begin with positioning the sensor in vivo and in contact with a body fluid such as ISF, and/or with the initiation (or powering on to full operational mode) of the on-body electronics. Initialization of on-body electronics may be implemented with a command generated and transmitted by a display device in response to the activation of a switch and/or by placing the display device within a predetermined distance (e.g., close proximity) to the on-body electronics, or by user manual activation of a switch on the on-body electronics unit, e.g., depressing a button, or such activation may be caused by the insertion device, e.g., as described in U.S. Publications 2010/0324392, 2011/0106126, 2011/0190603, 2011/0191044, 2011/0082484, 2011/0319729, and 2012/0197222, the disclosures of each of which are incorporated herein by reference for all purposes.

When initialized in response to a received command from a display device, the on-body electronics retrieves and executes, from its memory, a software routine to fully power on the components of the on-body electronics, effectively placing the on-body electronics in full operational mode in response to receiving the activation command from the display device. For example, prior to the receipt of the command from the display device, a portion of the components in the on-body electronics may be powered by its internal power supply, such as a battery, while another portion of the components in the on-body electronics may be in a powered down mode or a low power, inactive mode, or all components may be in a low power, inactive mode or a powered down mode. Upon receipt of the command, the remaining portion (or all) of the components of the on-body electronics is switched to an active, fully operational mode.

Embodiments of the on-body electronics may include one or more printed circuit boards with electronics including control logic implemented in ASIC, microprocessors, memory, and the like, and transcutaneously or subcutaneously positionable analyte sensors forming a single assembly. On-body electronics may be configured to provide one or more signals or data packets associated with a monitored analyte level upon detection of a display device of the analyte monitoring system within a predetermined proximity for a period of time (for example, about 2 minutes, 1 minute or less, about 30 seconds or less, about 10 seconds or less, about 5 seconds or less, or about 2 seconds or less) and/or until a confirmation, such as an audible and/or visual and/or tactile (e.g., vibratory) notification, is output on the display device indicating successful acquisition of the analyte related signal from the on-body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on-body electronics, but in many embodiments will be accomplished with display device electronics. In certain embodiments, glucose level is derived from the monitored analyte level in the ISF.

Analyte sensors may be insertable into a vein, artery, or other portion of the body containing the analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments of In Vivo Analyte Monitoring Systems

Figure 2A:
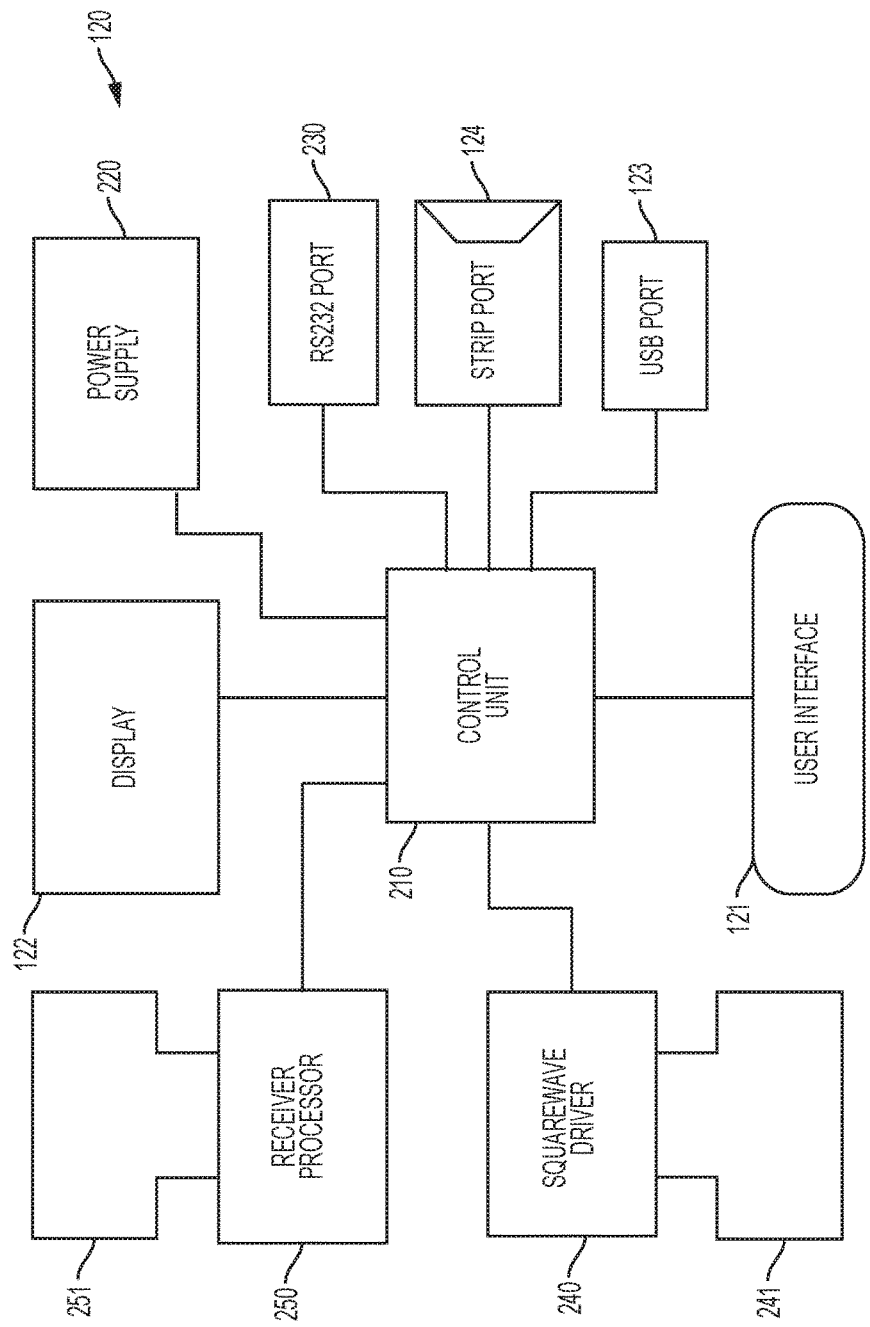
FIGS. 2A-B are block diagrams depicting example embodiments of a display device.
Figure 2B:
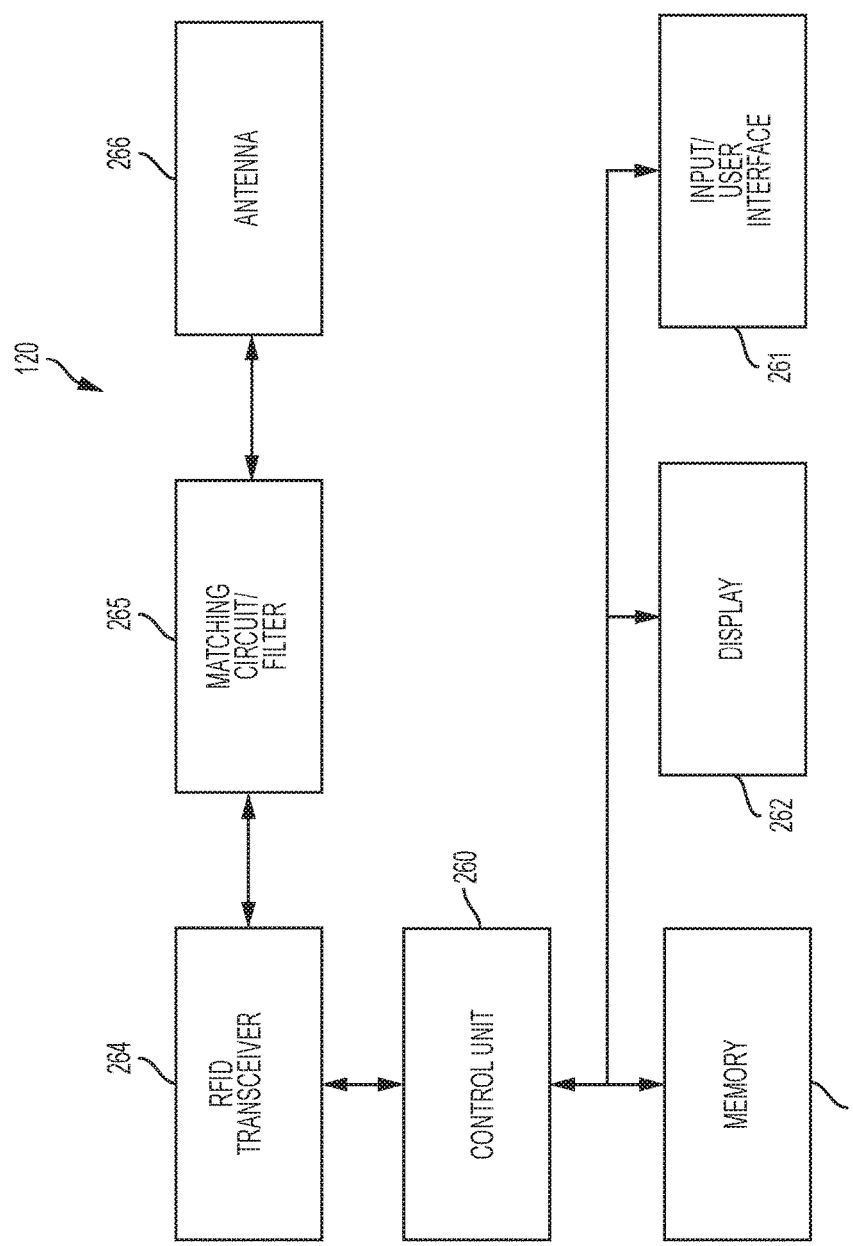

FIGS. 1 and 2A-B and their description are generally reproduced from US Patent Application Publ. No. 2011/0213225 (the '225 Publication), which is incorporated by reference herein in its entirety for all purposes. This '225 Publication describes systems, devices (e.g., on-body electronics device, display device/reader, etc.), and methods with and/or in which the power supply connection control circuits described herein can be used.

FIG. 1 is an illustrative view depicting an example embodiment of an in vivo-based analyte monitoring system 100. As shown, in certain embodiments, analyte monitoring system 100 includes on-body electronics 110 electrically coupled to in vivo analyte sensor 101 (a proximal portion of which is shown in FIG. 1) and attached to adhesive layer 140 for attachment on a skin surface on the body of a user. On-body electronics 110 includes on-body housing 119, which defines an interior compartment.

Also shown in FIG. 1 is insertion device 150 that, when operated, transcutaneously positions a portion of analyte sensor 101 through a skin surface and in fluid contact with ISF, and positions on-body electronics 110 and adhesive layer 140 on a skin surface. In certain embodiments, on-body electronics 110, analyte sensor 101, and adhesive layer 140 are sealed within the housing of insertion device 150 before use, and in certain embodiments, adhesive layer 140 is also sealed within the housing or itself provides a terminal seal of the insertion device 150. Devices, systems, and methods that may be used with the embodiments described herein are set forth in, e.g., U.S. Publications 2010/0324392, 2011/0106126, 2011/0190603, 2011/0191044, 2011/0082484, 2011/0319729, and 2012/0197222, the disclosures of each of which are incorporated herein by reference for all purposes.

Referring back to FIG. 1, analyte monitoring system 100 also includes display device 120, which includes a display 122 to output information to the user and/or to accept an input from the user (e.g., if configured as a touch screen), and an input component 121 such as a button, actuator, a touch sensitive switch, a capacitive switch, pressure sensitive switch, jog wheel or the like, to input data or commands to display device 120 or otherwise control the operation of display device 120. It is noted that some embodiments may include display-less devices or devices without any user interface components. These devices may be functionalized to store data as a data logger and/or provide a conduit to transfer data from an on-body electronics device and/or a display-less device to another device and/or location.

In certain embodiments, on-body electronics 110 may be configured to store some or all of the monitored analyte related data received from analyte sensor 101 in a memory during the monitoring time period, and maintain it in memory until the usage period ends. In such embodiments, stored data is retrieved from on-body electronics 110 at the conclusion of the monitoring time period, for example, after removing analyte sensor 101 from the user by detaching on-body electronics 110 from the skin surface where it was positioned during the monitoring time period. In such data logging configurations, a real time monitored analyte level is not communicated to display device 120 during the monitoring period or otherwise transmitted from on-body electronics 110, but rather, retrieved from on-body electronics 110 after the monitoring time period.

In certain embodiments, input component 121 of display device 120 may include a microphone and display device 120 may include software configured to analyze audio input received from the microphone, such that functions and operation of the display device 120 may be controlled by voice commands. In certain embodiments, an output component of display device 120 includes a speaker (not shown) for outputting information as audible signals. Similar voice responsive components such as a speaker, microphone, and software routines to generate, process, and store voice driven signals may be provided with on-body electronics 110.

In certain embodiments, display 122 and input component 121 may be integrated into a single component, such as a touch screen user interface or other display that can detect the presence and location of a physical contact. In such embodiments, the user may control the operation of display device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 120 also includes data communication port 123 for wired data communication with external devices such as remote terminal (personal computer) 170. Example embodiments of the data communication port 123 include a USB port, mini USB port, RS-232 port, Ethernet port, Firewire port, or other similar data communication port configured to connect to the compatible data cables. Display device 120 may also include an integrated in vitro glucose meter, including in vitro test strip port 124 to receive an in vitro glucose test strip for performing in vitro blood glucose measurements.

Referring still to FIG. 1, display 122 in certain embodiments is configured to display a variety of information—some or all of which may be displayed at the same or different time on display 122. The displayed information can be user-selectable so that a user can customize the information shown on a given display screen. Display 122 may include, but is not limited to: graphical display 138, for example, providing a graphical output of glucose values over a monitored time period (which may show markers such as meals, exercise, sleep, heart rate, blood pressure, etc.); numerical display 132, for example, providing monitored glucose values (acquired or received in response to the request for the information); and trend or directional arrow display 131 that indicates a rate of analyte change and/or a rate of the rate of analyte change, e.g., by moving locations on display 122.

As further shown in FIG. 1, display 122 may also include: date display 135, which can provide date information for the user; time of day information display 139 providing time of day information to the user; battery level indicator display 133 graphically showing the condition of the battery (rechargeable or disposable) of the display device 120; sensor calibration status icon display 134, for example, in monitoring systems that require periodic, routine or a predetermined number of user calibration events notifying the user that the analyte sensor calibration is necessary; audio/vibratory settings icon display 136 for displaying the status of the audio/vibratory output or alarm state; and wireless connectivity status icon display 137 that provides indication of wireless communication connection with other devices such as on-body electronics, data processing module 160, and/or remote terminal 170. As additionally shown in FIG. 1, display 122 may further include simulated touch screen buttons 125, 126 for accessing menus, changing display graph output configurations or otherwise for controlling the operation of display device 120.

Referring back to FIG. 1, in certain embodiments, display 122 of display device 120 can be configured to output alarms, alert notifications, glucose values, etc., which may be visual, audible, tactile, or any combination thereof. In one aspect, the display device 120 may include other output components such as a speaker, vibratory output component, and the like to provide audible and/or vibratory output indications to the user in addition to the visual output indications provided on display 122. Further details and other display embodiments can be found in, e.g., U.S. Publication 2011/0193704, which is incorporated herein by reference for all purposes.

After the positioning of on-body electronics 110 on the skin surface and analyte sensor 101 in vivo to establish fluid contact with ISF (or other appropriate body fluid), on-body electronics 110 in certain embodiments is configured to wirelessly communicate analyte related data (such as, for example, data corresponding to monitored analyte level and/or monitored temperature data, and/or stored historical analyte related data) when on-body electronics 110 receives a command or request signal from display device 120. In certain embodiments, on-body electronics 110 may be configured to at least periodically broadcast real time data associated with a monitored analyte level that is received by display device 120 when display device 120 is within communication range of the data broadcast from on-body electronics 110, i.e., it does not first need a command or request from a display device to send information.

For example, display device 120 may be configured to transmit one or more commands to on-body electronics 110 to initiate data transfer, and in response, on-body electronics 110 may be configured to wirelessly transmit stored analyte data collected during the monitoring time period to display device 120. Display device 120 may in turn be connected to a remote terminal 170, such as a personal computer, and may function as a data conduit to transfer the stored analyte level information from the on-body electronics 110 to remote terminal 170. In certain embodiments, the received data from the on-body electronics 110 may be stored (permanently or temporarily) in one or more memories of the display device 120. In certain other embodiments, display device 120 is configured as a data conduit to pass the data received from on-body electronics 110 to remote terminal 170, which is connected to display device 120.

Referring still to FIG. 1, also shown in analyte monitoring system 100 are data processing module 160 and remote terminal 170, both of which are optional. Remote terminal 170 may include a personal computer, a server terminal, a laptop computer, a tablet, or other suitable data processing devices including software for data management and analysis and communication with the components in analyte monitoring system 100. For example, remote terminal 170 may be connected to a local area network (LAN), a wide area network (WAN), or other data network for uni-directional or bi-directional data communication with display device 120 and/or data processing module 160.

The hardware, software, and functionality of the data processing device 160 can be performed by a discrete device as shown in FIG. 1 or incorporated within display device 120 or on-body electronics device 110.

Remote terminal 170 in certain embodiments may include one or more computer terminals located at a physician's office or a hospital. For example, remote terminal 170 may be located at a location other than the location of display device 120. Remote terminal 170 and display device 120 could be in different rooms or different buildings. Remote terminal 170 and display device 120 could be at least about one mile apart, e.g., at least about 10 miles apart, e.g., at least about 100 miles apart. For example, remote terminal 170 could be in the same city as display device 120, remote terminal 170 could be in a different city than display device 120, remote terminal 170 could be in the same state as display device 120, remote terminal 170 could be in a different state than display device 120, remote terminal 170 could be in the same country as display device 120, or remote terminal 170 could be in a different country than display device 120.

In certain embodiments, a separate, optional data communication/processing device such as data processing module 160 may be provided in analyte monitoring system 100. Data processing module 160 may include components to communicate using one or more wireless communication protocols such as, for example, but not limited to, an infrared (IR) protocol, Bluetooth protocol, Zigbee protocol, and an 802.11 wireless LAN protocol. Further description of communication protocols including those based on Bluetooth and/or Zigbee can be found in U.S. Patent Publication No. 2006/0193375, which is incorporated herein by reference for all purposes. Data processing module 160 may further include communication ports, drivers, or connectors to establish wired communication with one or more of display device 120, on-body electronics 110, or remote terminal 170 including, for example, but not limited to USB connector and/or USB port, Ethernet connector and/or port, FireWire connector and/or port, or RS-232 port and/or connector.

In certain embodiments, data processing module 160 is programmed to transmit a polling or query signal to on-body electronics 110 at a predetermined time interval (e.g., once every minute, once every five minutes, or the like), and in response, receive the monitored analyte level information from on-body electronics 110. Data processing module 160 stores in its memory the received analyte level information, and/or relays or retransmits the received information to another device such as display device 120. More specifically, in certain embodiments data processing module 160 may be configured as a data relay device to retransmit or pass through the received analyte level data from on-body electronics 110 to display device 120 or remote terminal 170 (for example, over a data network such as a cellular or WiFi data network) or both.

In certain embodiments, on-body electronics 110 and data processing module 160 may be positioned on the skin surface of the user within a predetermined distance of each other (for example, about 1-12 inches, or about 1-10 inches, or about 1-7 inches, or about 1-5 inches), such that periodic communication between on-body electronics 110 and data processing module 160 is maintained. Alternatively, data processing module 160 may be worn on a belt or clothing item of the user, such that the desired distance for communication between on-body electronics 110 and data processing module 160 for data communication is maintained. In a further aspect, the housing of data processing module 160 may be configured to couple to or engage with on-body electronics 110, such that the two devices are combined or integrated as a single assembly and positioned on the skin surface. In further embodiments, data processing module 160 is detachably engaged or connected to on-body electronics 110 providing additional modularity such that data processing module 160 may be optionally removed or reattached as desired.

Referring again to FIG. 1, in certain embodiments, data processing module 160 is programmed to transmit a command or signal to on-body electronics 110 at a predetermined time interval, such as once every minute, once every 5 minutes, once every 30 minutes, or any other suitable or desired programmable time interval to request analyte related data from on-body electronics 110. When data processing module 160 receives the requested analyte related data, it stores the received data. In this manner, analyte monitoring system 100 may be configured to receive the continuously monitored analyte related information at the programmed or programmable time interval, which is stored and/or displayed to the user. The stored data that is in data processing module 160 may subsequently be provided or transmitted to display device 120, remote terminal 170, or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider, or the user may adjust or recommend modification to the diet, daily habits and routines such as exercise, and the like.

In another embodiment, data processing module 160 transmits a command or signal to on-body electronics 110 to receive the analyte related data in response to a user activation of a switch provided on data processing module 160 or a user initiated command received from display device 120. In further embodiments, data processing module 160 is configured to transmit a command or signal to on-body electronics 110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 160 may be programmed to automatically transmit a request, command, or signal to on-body electronics 110. Alternatively, data processing module 160 may be programmed to activate an alarm to notify the user that a predetermined period of time has elapsed since the last communication between data processing module 160 and on-body electronics 110. In this manner, users or healthcare providers may program or configure data processing module 160 to provide certain compliance with the analyte monitoring regimen, so that frequent determination of analyte levels is maintained or performed by the user.

In certain embodiments, when a programmed or programmable alarm condition is detected (for example, a detected glucose level monitored by analyte sensor 101 that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition)), the one or more output indications may be generated by the control logic or processor of on-body electronics 110 and output to the user on a user interface of on-body electronics 110 so that corrective action may be taken. In addition to, or alternatively, if display device 120 is within communication range, the output indications or alarm data may be communicated to display device 120 whose processor, upon detection of the alarm data reception, controls the display 122 to output one or more notification.

In certain embodiments, control logic or microprocessors of on-body electronics 110 include software programs to determine future or anticipated analyte levels based on information obtained from analyte sensor 101, e.g., the current analyte level, the rate of change of the analyte level, the acceleration of the analyte level change, and/or analyte trend information determined based on stored monitored analyte data providing a historical trend or direction of analyte level fluctuation as function time during the monitored time period. Predictive alarm parameters may be programmed or programmable in display device 120, or the on-body electronics 110, or both, and output to the user in advance of anticipating the user's analyte level reaching the future level. This provides the user an opportunity to take timely corrective action.

Information, such as a variation or fluctuation of the monitored analyte level as a function of time over the monitored time period that provides analyte trend information, for example, may be determined by one or more control logic or microprocessors of display device 120, data processing module 160, remote terminal 170, and/or on-body electronics 110. Such information may be displayed as, for example, a graph (such as a line graph) to indicate to the user the current, historical, and/or and predicted future analyte levels as measured and predicted by the analyte monitoring system 100. Such information may also be displayed as directional arrows (for example, see trend or directional arrow display 131) or other icon(s), e.g., the position of which on the screen relative to a reference point indicate whether the analyte level is increasing or decreasing, as well as the acceleration or deceleration of the increase or decrease in the analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as a means of notifying the user of the current level, direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on-body electronics 110, remote terminal 170, or display device 120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit), and configured for performing data processing or data upload/download over the internet. In such embodiments, remote terminal 170 may be configured to provide the executable application software to the one or more of the communication devices described above when communication between the remote terminal 170 and the devices are established.

Embodiments of Display Devices

FIG. 2A is a block diagram of display device (or reader) 120 as shown in FIG. 1. Display device 120 includes control unit 210, which can be one or more controllers, microcontrollers, processors, and/or microprocessors, operatively coupled to a display 122 and a user interface 121. Display device 120 may also include one or more data communication ports such as a USB port (or connector) 123 or RS-232 port 230 (or any other wired communication ports) for data communication with data processing module 160, remote terminal 170, on-body electronics 110, or other devices such as a personal computer, a server, a mobile computing device, a mobile telephone, a pager, or other handheld data processing devices including mobile telephones such as internet connectivity enabled smart phones, with data communication and processing capabilities including data storage and output. Additional details of display device 120 and other components of analyte monitoring system 100 are provided in U.S. Patent Appl. Publ. Nos. 2010/0198034, 2010/0198142, 2010/0265073, and 2011/0256024, the disclosures of each of which are incorporated by reference herein in their entirety for all purposes.

Display device 120 may include a strip port 124 configured to receive in vitro test strips (not shown). Strip port 124 can be coupled to control unit 210, which can include programming to process the sample on the in vitro test strip received in the strip port 124. Any suitable in vitro test strip may be employed, e.g., test strips that only require a very small amount (e.g., one microliter or less, e.g., about 0.5 microliter or less, e.g., about 0.1 microliter or less), of sample applied to the strip in order to obtain accurate glucose information, e.g., FreeStyle® or Precision® blood glucose test strips and systems from Abbott Diabetes Care Inc. Display devices with integrated in vitro monitors and test strip ports may be configured to conduct in vitro analyte monitoring with no user calibration in vitro test strips (i.e., no human intervention calibration), such as FreeStyle Lite glucose test strips from Abbott Diabetes Care Inc.

In certain embodiments, an integrated in vitro meter can accept and process a variety of different types of test strips (e.g., those that require user calibration and those that do not), some of which may use different technologies (those that operate using amperometric techniques and those that operate using coulometric techniques), etc. Detailed description of such test strips and devices for conducting in vitro analyte monitoring is provided in U.S. Pat. Nos. 6,377,894, 6,616,819, 7,749,740, 7,418,285 and in U.S. Patent Appl. Publ. Nos. 2004/0118704, 2006/0091006, 2008/0066305, 2008/0267823, 2010/0094110, 2010/0094111, 2010/0094112, and 2011/0184264, the disclosure of each of which are incorporated herein by reference for all purposes. The present subject matter can be used with and/or in the systems, devices, and methods described in these incorporated references.

Glucose information obtained by the in vitro glucose testing device may be used for a variety of purposes, computations, etc. For example, the information may be used to calibrate analyte sensor 101 (FIG. 1) if the sensor requires in vivo calibration, confirm results of analyte sensor 101 to increase the confidence in the results from sensor 101 indicating the monitored analyte level (e.g., in instances in which information obtained by sensor 101 is employed in therapy related decisions), etc. In certain embodiments, analyte sensors do not require calibration by human intervention during its usage life. However, in certain embodiments, a system may be programmed to self-detect problems and take action, e.g., shut off and/or notify a user. For example, an analyte monitoring system may be configured to detect system malfunction, a potential degradation of sensor stability, or a potential adverse condition associated with the operation of the analyte sensor, the system may notify the user, using display device 120, to perform analyte sensor calibration or compare the results received from the analyte sensor corresponding to the monitored analyte level, to a reference value (such as a result from an in vitro blood glucose measurement).

In certain embodiments, when the potential adverse condition associated with the operation of the sensor, and/or potential sensor stability degradation condition is detected, the system may be configured to shut down (automatically without notification to the user, or after notifying the user) or disable the output or display of the monitored analyte level information received the on-body electronics assembly. In certain embodiments, the analyte monitoring system may be shut down or disabled temporarily to provide an opportunity to the user to correct any detected adverse condition or sensor instability. In certain other embodiments, the analyte monitoring system may be permanently disabled when the adverse sensor operation condition or sensor instability is detected, including by disconnecting the power source using a control circuit as described herein.

Referring still to FIG. 2A, power supply 220, such as one or more batteries, rechargeable or single use disposable, is also provided and operatively coupled to control unit 210, and configured to provide the necessary power to display device 120 for operation. In addition, display device 120 may include an antenna 251 such as a 433 MHz (or other equivalent) loop antenna, 13.56 MHz antenna, or a 2.45

GHz antenna, coupled to a receiver processor 250 (which may include a 433 MHz, 13.56 MHz, or 2.45 GHz transceiver chip, for example) for wireless communication with the on-body electronics 110 (FIG. 1). Additionally, an inductive loop antenna 241 is provided and coupled to a square wave driver 240 that is operatively coupled to control unit 210. Display device 120 can send and/or receive signals or data to on-body electronics 110 using any of the near field communication (NFC), Bluetooth, or Bluetooth Low Energy (BTLE) communication protocols in existence as of the date of this filing or later developed.

In certain embodiments, antenna configurations including loop antenna configurations are provided for display device 120 for data communication at Ultra High Frequency (UHF) frequency bands. These can be used in a real time analyte data acquisition system that includes display device 120 configured to generate a strong near electromagnetic field to provide power to on-body electronics 110 for the purpose of receiving sampled and/or processed analyte related data from on-body electronics 110. Such configuration also provides a weak far electromagnetic field such that the strength of the generated magnetic field at a far distance, such as about 3 meters away or 4 meters away or more from on-body electronics 110, that maintains the data communication range between on-body electronics 110 and display device 120. In certain embodiments, display device 120 may be configured for RF transmission at any frequency.

FIG. 2B illustrates a block diagram of another example embodiment of display device 120 in the analyte monitoring system 100. Display device 120 includes control unit 260 operatively coupled to input/user interface 261, display 262, memory 263, and RFID transceiver 264, which is adapted for communication with, e.g., on-body electronics 110. RFID transceiver 264 can be operatively coupled to matching circuit/filter 265, which is in turn coupled to antenna 266. Matching circuit/filter 265 can be configured to tune and/or match the signals between the on-body electronics 110 and display device 120, sent and received via antenna 266. Antenna 266, in certain embodiments includes a 13.56 MHz RFID antenna where RFID transceiver 264 is configured to operate in the 13.56 MHz frequency. In certain embodiments, RFID transceiver 264 may include a user programmable modulation depth in a write mode where data or commands are sent, whereas single subcarrier, frequency shift keying (FSK) and phase shift keying (PSK) modulations are recognized in a read mode where data is received from on-body electronics 110. Moreover, a logarithmic amplifier may be used for single subcarrier detection for data recovery from on-body electronics 110.

As with control unit 210 described with respect to FIG. 2A, control unit 260 can be one or more controllers, microcontrollers, processors, and/or microprocessors. Control unit 260 (and 210) can also be implemented as an ASIC with programmed logic that is executable by one or more state machines for controlling and executing the operation of display device 120. Memory 263 in certain embodiments includes non-transitory volatile memory and/or non-transitory non-volatile memory for data storage.

In certain embodiments, data communication between on-body electronics 110 and display device 120 may be achieved at the 2.45 GHz ISM band. In certain embodiments, display device 120 is configured to listen for a clear channel on 2.45 GHz radio frequency band. When a clear channel is detected and selected, a clear channel identifier is sent to a control unit of on-body electronics 110. After the clear channel identifier is received, the data packets are provided to the receiver unit. Thus, the power drain of the "listen before talk" process required of operation in the 2.45 GHz ISM band comes off of the larger batteries in display device 120, conserving power in on-body electronics 110.

Embodiments of Power Supply Connection Control Circuits

Figure 3A:
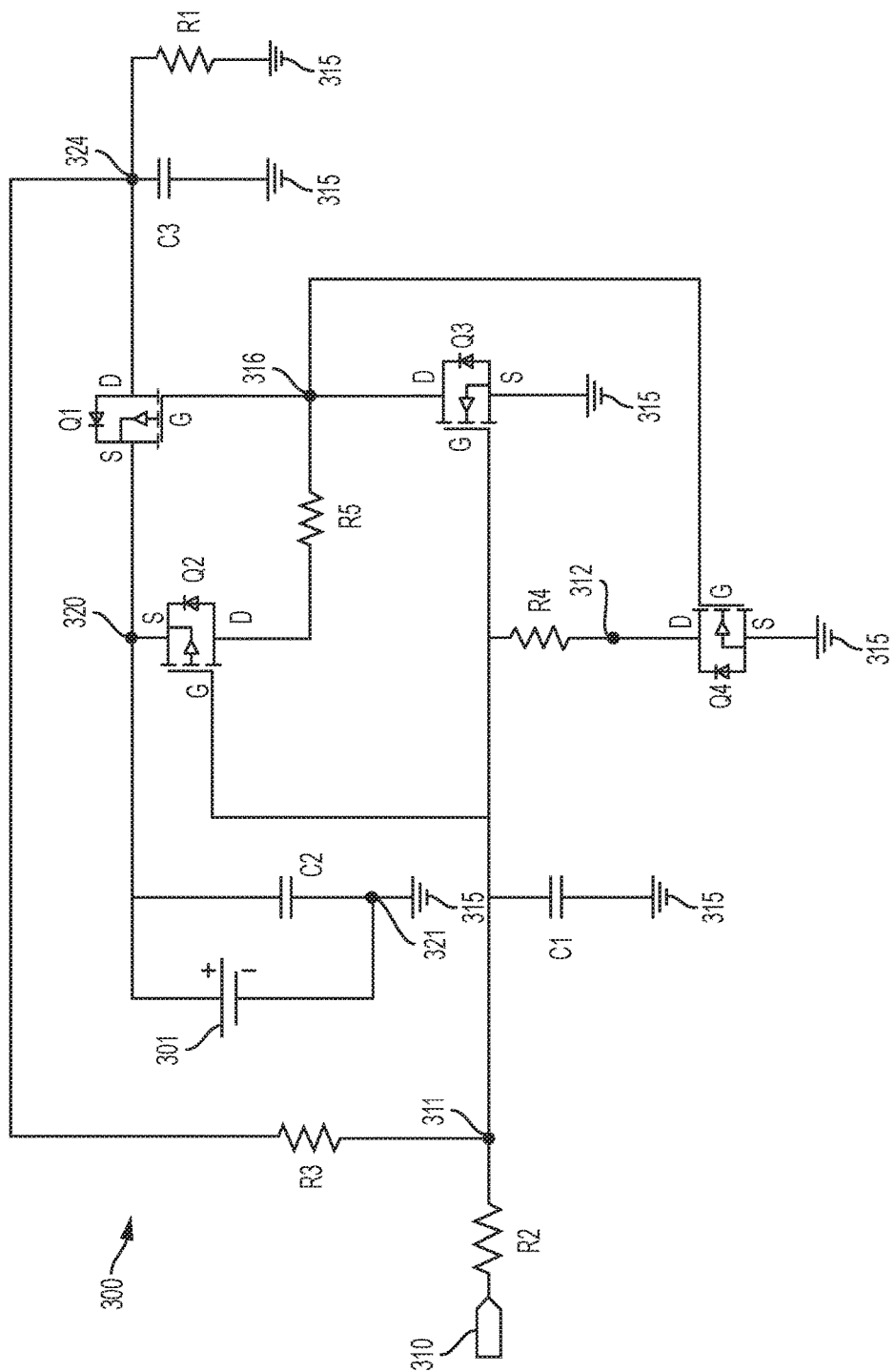
FIGS. 3A-C are schematic diagrams depicting example embodiments of a power supply control circuit.

FIG. 3A is an electrical schematic of an example embodiment of a power supply control circuit 300. Here, a power supply 301 is shown coupled with circuitry that can be used to control, or manage, whether power supply 301 is electrically coupled with a load R1 of the overall device, which can be, for example, display device 120 or on-body electronics 110. A first input node 310 is coupled with a resistor R2, the opposite terminal of which forms another node 311. A control signal for controlling the state of connection of power supply 301 can be propagated into input node 310. Alternatively, node 311 can be viewed as the input node.

In this embodiment, four transistors Q1-Q4 are included within control circuit 300, although more or less transistors can be used. Transistors Q1 and Q2 are P-type MOSFETs (PMOS), and transistors Q3 and Q4 are N-type MOSFETs (NMOS). Those of ordinary skill in the art will readily recognize other arrangements of PMOS and NMOS transistors that can be used to perform functions similar to those described herein for circuit 300. Each transistor is shown with a bulk connection to its source and a body diode (oriented to block drain-to-source current for the NMOS arrangement and source-to-drain current for the PMOS arrangement).

While enhanced MOSFETs are depicted in FIG. 3A, it should be noted that other types of field effect transistors (FETs) can be used as well, with modifications as will be apparent to those of ordinary skill in the art. Those other transistor types include, but are not limited to, JFET, MOSFET without bulk, MOSFET depleted, MESFET, or IGFET. Processes with low gate leakages and low drain-source leakages are particularly suitable for use with the control circuit embodiments described herein.

Node 311 is coupled with a gate node of transistor Q3, a resistor R3, a capacitor C1, a resistor R4, and a gate of transistor Q2. The opposite terminal of resistor R4 is coupled with node 312, which in turn is coupled with a drain of transistor Q4. The source of transistor Q4 is coupled with a reference node 315, e.g., ground.

A gate of transistor Q4 is coupled with node 316. Node 316 is coupled with a drain of transistor Q3, while a source of transistor Q3 is coupled with reference node 315. Node 316 is also coupled with a resistor R5 and a gate of a transistor Q1.

The opposite terminal of resistor R5 is coupled with a drain of transistor Q2. A source of transistor Q2 is coupled with node 320, which is also coupled with a source of transistor Q1 and a positive terminal of power supply 301. The negative terminal of power supply 301 is coupled with node 321 and a capacitor C2 is coupled between nodes 320 and 321. Node 321 is coupled with reference node 315.

A drain of transistor Q1 is coupled with node 324, which in turn is coupled with electrical load R1, capacitor C3, and the opposite terminal of resistor R3 (the first terminal being coupled with node 311 as mentioned earlier). The opposite terminals of capacitor C3 and resistor R1 are coupled with reference node 315.

It should be noted that while control circuit 300 has been described with respect to the presence of electrical nodes (e.g., 310, 311, 312, etc.), these nodes are indicative of common electrical connections and are used for illustrative purposes only. One of ordinary skill in the art will readily recognize that these nodes do not necessarily constitute "additional components" and can be viewed merely as an electrical connection, which can be formed by any conductor (e.g., a metal trace, a via, a pad, an external lead, a wire, and the like).

Turning to the operation of control circuit 300, the state of connection or disconnection of power supply 301, henceforth referred to as a battery 301, can be accomplished by the voltage applied to input node 310. Input node 310 can be coupled to the power actuator for the device (e.g., an ON/OFF button) through hardware only, such that control circuit 300 can connect battery 301 without requiring a command to do so from a processor, controller, or any other software executing circuit that requires power to issue a command. Typically, it is only upon connection of battery 301 that a resident processor will be supplied with power, and only then is the processor able to boot up its software and begin issuing commands. Circuitry capable of initiating the battery connection without software intervention can therefore be included in circuit 300.

However, in some embodiments, power can be supplied to display device 120 before the connection of battery 301. For example, the user can connect display device 120 to another power source, such as a personal computer or tablet through a wired connection (e.g., a USB cable, etc.). Display device 120 can be configured to draw power from the other source and activate (e.g., boot up) any on-board software-executing circuit (e.g., a processor, controller, etc.), which can then be used to issue commands to control circuit 300. Thus, input node 310 can, in some embodiments, be coupled to an input/output (I/O) line of a software-executing circuit resident in the device on which control circuit 300 resides, for instance, control unit 210 (FIG. 2A) or control unit 260 (FIG. 2B). The control unit can be adapted to drive input node 310 high, i.e., with a relatively high voltage, to initiate the transition of battery 301 from a disconnected state to a state in which it is connected and capable of supplying current to device load R1. Control circuit 300 can be fabricated in the same silicon chip as the software-executing circuit, or can be implemented on a separate chip, located in the same silicon package or a different package.

Control unit 210 or 260 can drive input node 310 high or low in response to any number of conditions. In one embodiment, control unit 210 or 260 recognizes connection of the overall device to a secondary power source (e.g., a computer via a USB cable), and drives input node 310 high in response thereto. In another embodiment, after battery 301 is already connected, control unit 210 or 260 recognizes that display device 120 has not been used for a lengthy period of time, and drives input node 310 low to disconnect battery 301. In yet another embodiment, the user performs a "long push" of the power button, where the holding of the power button down by the user for a predetermined amount of time is interpreted as a command to, if initially in the powered on state, disconnect battery 301 from the load. Control unit 210 or 260 can also drive input node 310 high or low in response to a command received on the control unit's I/O interface.

In certain embodiments, the device in which control circuit 300 is resident, such as display device 120, can have multiple modes of operation each having different conditions for the connection and disconnection of battery 301. In one embodiment, display device 120 has a first mode where battery 301 is disconnected upon the powering down of display device 120, and a second mode where battery 301 remains connected even after powering down display device 120. For example, after connection to a secondary power source, display device 120 can boot up into an initial setup mode (or pre-setup mode), where software, calibration parameters, or other data can be uploaded to display device 120 by the manufacturer to configure device 120 with the appropriate functionality and settings for use. Activation of display device 120 in this pre-setup mode will direct control circuit 300 to connect battery 301 immediately either with the intervention of software or through a hardware-only circuit. Once display device 120 has completed the software boot up, it can be inspected, further configured or reconfigured, or otherwise tested or manipulated prior to shipment. So long as the initial setup is not completed, display device 120 can remain in the pre-setup mode and control unit 210 or 260 (using software) can command control circuit 300 to disconnect battery 301 upon the deactivation or powering down of display device 120.

If the initial setup is completed, such as by a user upon the initial use of display device 120 in the field, then display device 120 can enter a second, post-setup mode, in which display device 120 will remain during normal operation by the user. In this post-setup mode, activation of device 120 will connect battery 301 in a manner similar to that of the pre-setup mode. However, upon an instruction to deactivate display device 120, such as by pressing the off button, control unit 210 or 260 will not instruct control circuit 300 to disconnect battery 301. Instead, it will remain connected while display device 120 is off.

In certain embodiments, while display device 120 is in the post-setup mode, and even if deactivated (off), the display device software can continue to monitor battery 301 and disconnect it if the power level drops below a predetermined threshold, e.g., one that can safely operate the device. Also, the display device software can monitor the length of time that has passed since the last use. The software can cause battery 301 to be disconnected if a set time has passed (e.g., 7 days, 2 weeks, 3 weeks, etc.) since the last use of display device 120. In another embodiment, the software can cause battery 301 to be disconnected if both a set time has passed since the last use and display device 120 has not yet established a connection with on-body electronics 110 (e.g., has not yet been paired).

The operation of this example embodiment of circuit 300 will now be further described by reference to the various individual circuit components. To connect battery 301, input node 310 is driven high, resulting in the application of a high-voltage across resistor R2 to the gate of transistor Q3, which activates Q3, i.e., turns it on, and allows current to flow between Q3's drain and source. This drives the voltage of node 316 towards that of reference node 315, e.g., low, which in turn applies a low voltage to the gate of transistor Q1. The low voltage activates Q1, allowing current to flow between the source and drain of Q1. The low voltage on node 316 also causes a low voltage to be applied to the gate of transistor Q4, thereby deactivating Q4, i.e., turning it off.

Current is then free to flow between the source and drain of transistor Q1. Battery 301 is electrically connected through transistor Q1 to node 324 and, thus, able to supply power to the load of the device R1. Control unit 210 or 260 can then optionally apply a high impedance to input node 310. The voltage feedback from node 324 through resistor R3 keeps node 311 at a high level, which in turn maintains Q3 in its activated (on) state and that, in turn, keeps transistor Q1 in its activated state. After a short time, capacitor C1 becomes fully charged through R2 and the R3 feedback path and Q2 is turned off, if not already deactivated by the application of the high-voltage to input node 310.

At this point, transistors Q1 and Q3 are activated and transistors Q2 and Q4 are deactivated. Battery 301 is maintained in a connected state even after removal of the voltage from input node 310. In this connected at-rest state, no significant resistive-only path exists between battery 301 and ground (node 315). The loads that exist between battery 301 and ground pass through the transistors and capacitors only. Because there is no resistive-only path from battery to ground, the leakage current of control circuit 300 is kept at a minimal level. This characteristic improves the suitability of these embodiments for use in applications where battery 301 remains connected to the electrical load at all times, even when the overall device is powered off.

Disconnection of battery 301 is accomplished in a similar fashion, but in reverse. A low voltage is applied to input node 310 and passes through resistor R2. Any charge on capacitor C1 is then drained. The voltage at node 311 becomes low and is applied to the gate of transistor Q3, which deactivates it (turns it off). The low voltage is also applied to the gate of transistor Q2, which activates it (turns it on). With Q2 activated, the voltage at node 316 is pulled towards the high voltage at node 320, which is applied to the gate of transistor Q1 and deactivates Q1. The high-voltage at node 316 is also applied to the gate of transistor Q4, activating Q4 and pulling down the voltage at node 311, which keeps transistor Q3 deactivated. Input node 310 can then be placed in a high impedance state, if desired. Transistors Q2 and Q4 remain activated and keep transistors Q1 and Q3 in a deactivated state. Again, there is no resistive-only loading to ground, and only small leakage currents are possible through the transistors and capacitors. Thus, the overall leakage current of control circuit 300 is kept at a minimal level.

Figure 3B:
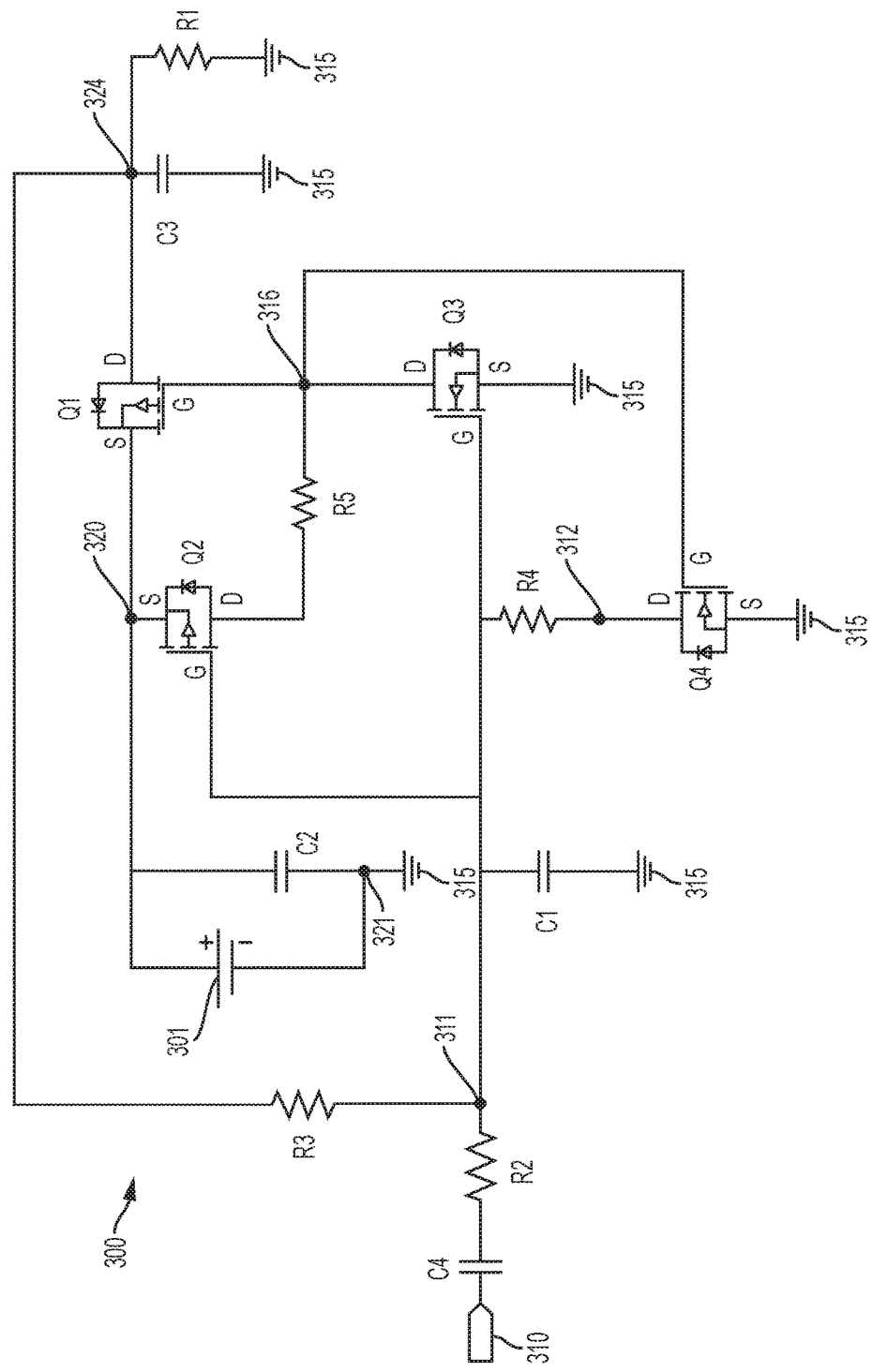

FIG. 3B is an electrical schematic of another example embodiment of power supply control circuit 300. Here, instead of using solely an input resistor R2, as with the embodiment described with respect to FIG. 3A, this embodiment includes an input capacitor C4 in series with resistor R2 for AC coupling at input node 310. The activation signal would still be a high (or high-going) pulse for connection and a low (or low-going) pulse for disconnection, but static or DC leakage would be eliminated or substantially eliminated by the presence of C4. This embodiment is particularly suitable for implementations lacking input/output (I/O) lines with high impedance capability, or for implementations having a high impedance capability but with undesirable leakage.

The following embodiment provides example values for the discrete components described with respect to FIG. 3A, in combination with modeled response times for the activation or deactivation of the transistors and charging or discharging of the capacitors. These example values are for the purpose of illustrating the performance of control circuit 300 in just one of many possible implementations. As stated earlier, and repeated here, in no way should these values be used to limit the scope of the claims, absent their explicit recitation therein.

In this example, the voltage of battery 301 can be in the range of 3.6 to 4.2 volts, although other voltages outside of this range can be used, provided that sufficient voltage can be generated to exceed the various gate-source thresholds of the transistors (typically 0.7 to 1.4 volts). Resistor R1 represents the resistance of the load of battery 301. A practical maximum current can be determined for circuit 300, such as based on the specifications of Q1, and used with the voltage of battery 301 (e.g., 4 volts) to determine the maximum resistive load R1 for circuit 300. For example, a 0.5 amp maximum current with a 4 volt battery would equate to a maximum load of 8 ohms ($\Omega$).

Capacitor C3 represents the capacitance of the load and, in one example, has a value of 0.1 micro-Farads ($\mu$F). The feedback resistor R3, along with capacitor C3, can determine the requisite width of an input pulse required to change the state of circuit 300 (e.g., connect or disconnect battery 301). In one example, R3 has a value of 100 K$\Omega$, which results in a time constant of 10 msecs (R3*C3). It can take approximately 3 time constants (30 msecs) to fully charge or discharge C3 (as will be explained below) and the input pulse is, in many embodiments, at least that long (for example, in one example the input pulse has a conservative duration of 50 msecs).

The resistance of input resistor R2 can be chosen to be much smaller than that of feedback resistor R3 in order to allow the input pulse at input node 310 to be the primary factor determining the state of Q3, which in turn controls the state of circuit 300. For example, the input pulse (through R2) can override the battery voltage (through R3) in order to disconnect battery 301. The value of R2, in certain embodiments, is chosen to be high enough to limit excessive current through any I/O pin connected to input node 310 when charging or discharging capacitor C1. In one example, R2 has a value of 1 K$\Omega$.

Capacitor C1 can be used to filter input noise, which can cause unintended state changes in circuit 300 (e.g., an inadvertent disconnection of battery 301). The capacitance of C1 can be chosen to be low enough such that the time constant with input resistor R2 is significantly shorter than the length of the input pulse (e.g., 50 msecs) to avoid filtering that pulse. In one example, C1 has a value of 0.1 $\mu$F.

If the input capacitor C4 is present (e.g., as depicted in FIG. 3B), then the value of C4 can be chosen to be 10-100 times the value of C1 in order to allow the full amplitude (or substantially the full amplitude) of the input pulse to be propagated to the gate of Q3, which can control circuit 300. Here, the voltage of the input pulse at node 310 is reduced at the gate node of Q3 by a factor of approximately C4/(C1+C4). When the input capacitor C4 is not present (e.g., as depicted in FIG. 3A), then the voltage of the input pulse is determined primarily by the relationship of R2 and R3 as already described.

Resistors R4 and R5 can be chosen to have a resistance that is low enough to minimize the gate-to-source voltage (Vgs) of Q3 and Q1 (due to gate-to-source leakage current passing through R4 and R5), respectively, when Q4 and Q2 are activated. Gate-to-source leakage increases with temperature. Uncontrolled voltages at the gates could interfere with the operation of transistors Q1 and Q3 (e.g., prematurely activating those transistors). However, this consideration should be balanced with the notion that R4 and R5 can also be chosen to have a high enough resistance, when compared to R2, to avoid significant attenuation of the input pulse when changing the state of circuit 300.

For example, R4 forms a voltage divider with R2 (e.g., R4/(R4+R2)) and when the input pulse is high (changing circuit 300 from a disconnected state to a connected state), this voltage divider attenuates the voltage of the input pulse at the gate of Q3, which should remain high enough to activate Q3 and cause the connection of battery 301. Likewise, a similar effect can occur with R5, where it can form a voltage divider with R2 when the input pulse is low (changing circuit 300 from a connected state to a disconnected state). In one example, R4 and R5 are 10 K$\Omega$, which is approximately one order of magnitude (10x) higher than R2 when set at 1 K$\Omega$.

Capacitance C2 can be the desired capacitance placed across battery 301. In certain embodiments, it is placed on the input side of Q1 (e.g., the source node for a PFET) so that it does not add to the capacitance of C3, which would increase the time constant with R3 and require longer input pulses to cause a state change in circuit 300.

Several examples of sequences of events for changing the state of circuit 300 are provided. To connect battery 301, the voltage at node 310 is driven high for 50 msecs. R2 and C1 form an RC time constant at the gate of Q3 of 0.1 msecs (1 KΩ*0.1 µF) and Q3 is fully activated in about 0.5 msecs. This activates Q1 and deactivates Q4. Q2 may remain activated for the time being due to a −1V gate-to-source voltage. Input node 310 is then set to a high impedance state. The feedback through R3 keeps Q3 and Q1 activated. After about 50 msecs, C1 is fully charged up to the battery voltage through R3 (10 msec time constant) and this deactivates Q2. This example provides a relatively fast response time, allowing battery 301 to be connected to the load within 0.05 seconds of, e.g., the user pushing the activation button.

To disconnect battery 301, the voltage at node 310 is driven low for 50 msecs. Q3 is deactivated in about 0.5 msecs. Q2 is activated in about 0.5 msec, which keeps Q1 deactivated through the pull-up resistor R5 and, also, activates Q4, which, in turn, keeps Q3 deactivated through the pull down resistor R4. After 50 msecs, C3 is fully drained ((100 KΩ)*(0.1 µF)=10 msec time constant). Battery 301 is disconnected and input node 310 can then be set to a high impedance state if so desired.

As mentioned, in some embodiments, control circuit 300 can be implemented within a portable electronic device, including, but not limited to display device 120 or on-body electronics 110 in an in vivo system (that may also have in vitro test capability), or a dedicated in vitro meter (without in vivo analysis capability). Display device 120 is, in many embodiments, a dedicated use device (e.g., specialized to interface with on-body electronics 110) that is sold with the system for use by diabetics. However, as described in detail above, display device 120 can also be a communication device or personal computing device such as a smartphone or tablet.

For ease of illustration, the following embodiments are described with reference to the presence of control circuit 300 within display device 120 (which can also be referred to as a portable reader device). The resistive load of control circuit 300 (the load to which the power supply is connected/disconnected) can be any or all of the units depicted and/or described with respect to FIG. 2A including, but not limited to, control unit 210, display 122, user interface 121, square-wave driver 240, receiver processor 250, USB port 123, RS-232 port 230, strip port 124, antennas 241 and 251, and any combination thereof. Likewise, the resistive load of control circuit 300 can be any or all of the units depicted and/or described with respect to FIG. 2B including, but not limited to, control unit 260, input/user interface 261, display 262, memory 263, RFID transceiver 264 (or a Bluetooth, BTLE, or other NFC transmitter and/or receiver), matching circuit/filter 265, antenna 266, and any combination thereof.

Power supply (220, 301) of display device 120 can be contained within a housing of device 120 such that power supply (220, 301) is inaccessible to the user. Such may be the case with a size-minimized design, where battery accessibility requires too much physical space, or is rendered unnecessary with the use of control circuit 300.

Figure 3C:
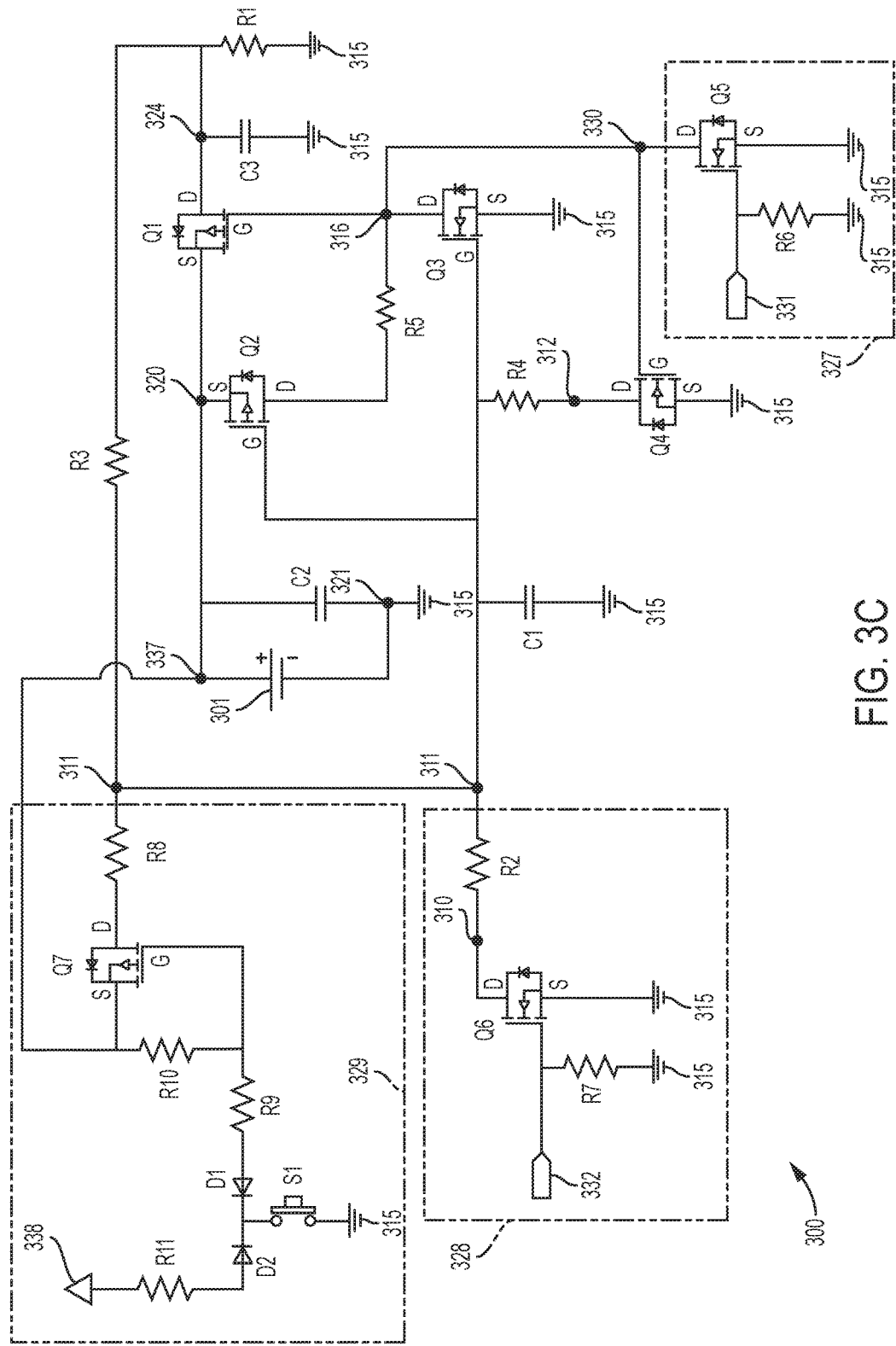

FIG. 3C depicts an example embodiment of control circuit 300, similar to that shown in FIG. 3A, but having various input controls 327-329 for controlling the connection and disconnection of battery 301. In this embodiment, input controls 327 and 328 are software input controls that can be connected to I/O lines of control unit 210 or 260. Input controls 327 and 328 can be used, for example, to buffer output pins of control unit 210 or 260 from what can be a higher battery voltage as compared to the power level seen by control unit 210 or 260. Controls 327 and 328 can be used with circuit 300 as depicted in FIG. 3A, and can form an alternative to the capacitive buffer (C4) depicted in FIG. 3B. In this embodiment, input control circuit 329 is a hardware input control that can be connected to an externally accessible button or switch.

Referring back to input control 327, it is one example of an embodiment used for connecting battery 301 when circuit 300 is in the disconnected state. Input control 327 has an input node 331 that can be coupled to an I/O line that provides a connection control signal. Input control 327 can include a transistor Q5 and a resistor R6 coupled between the gate node of Q5 and reference node 315. Input node 331 can be coupled directly to the gate node of Q5 as well. In this example, transistor Q5 is an NFET with a source node coupled to reference node 315 and a drain node coupled to the gate node of transistor Q1 at node 330. To cause the connection of battery 301, in this example, a high signal is pulsed from an I/O line into input node 331, which activates Q5 and drives node 330 low. In turn, the gate node of transistor Q1 is driven low, thereby activating Q1 and connecting battery 301 to the load (R1 and C3). To avoid any further effects on circuit 300, input node 331 can be set low, disabled, or placed into a high impedance state after the transmission of the high input connection pulse.

Input control 328, on the other hand, is one example of an embodiment used for disconnecting battery 301 when circuit 300 is in the connected state. Input control 328 has an input node 332 that can be coupled to an I/O line that provides a disconnection control signal. Input control 328 can include a transistor Q6 and a resistor R7 coupled between the gate node of Q6 and reference node 315. Input node 332 can be coupled directly to the gate node of Q6 as well. In this example, transistor Q6 is an NFET with a source node coupled to ground 315 and a drain node coupled to input node 310 of circuit 300, which leads to resistor R2. To cause the disconnection of battery 301, in this example, a high signal is pulsed at input node 332, which activates Q6 and drives input node 310 low. Circuit 300 can then cause the disconnection of battery 301 in the manner already described. As with input control 327, to avoid any further effects on circuit 300, input node 332 can be set low, disabled, or placed into a high impedance state after the transmission of the high input disconnection pulse.

A hardware-only embodiment for connecting battery 301 is provided by input control 329. Input control 329 can be actuated by an externally accessible actuator (or button, switch, etc.), which is referred to herein as switch S1, that can cause connection of battery 301 without any software driven commands sent from the I/O lines of control unit 210 or 260. Input control 329 can include a transistor Q7, multiple resistors R8-R11, and a pair of opposing diodes D1 and D2, which can be, but are not limited to, Schottky diodes.

A terminal of resistor R8 is coupled with node 311 (depicted twice for ease of illustration although it is one electrical node). In this example, transistor Q7 is a PFET with a drain node coupled with the opposite terminal of resistor R8. A source node of Q7 is coupled with the positive terminal of battery 301 and a terminal of resistor R10. The opposite terminal of resistor R10 is coupled with a gate node of Q7, which is also coupled with a terminal of resistor R9. The opposite terminal of resistor R9 is coupled with an anode of diode D1. A cathode of diode D1 (the opposite terminal) is coupled with the cathode of diode D2 and a terminal of switch S1 (which can also be connected to electrostatic discharge (ESD) protection circuitry and the like). The closing of switch S1 causes the diode cathodes to each be connected to ground 315. An anode of diode D2 is coupled with a terminal of resistor R11, the opposite terminal of which is coupled with a voltage source 338 for other circuitry (e.g., control unit 210 or 260, etc.) that can be sourced from a separate power supply or can be a down-regulated voltage from battery 301. Diodes D1 and D2 act as blocking diodes between source 338 and battery 301. Source 338, resistor R11, and diode D2 act to generate a signal at the cathode of D2 that represents the state of switch S1 to control unit 210 or 260.

When battery 301 is disconnected and switch S1 is open, the battery (through R10) positively biases the gate node of transistor Q7 and maintains it in a deactivated (off) state. When switch S1 is closed by the user, diode D1 becomes forward biased and the gate node of transistor Q7 is pulled low (to ground 315), thereby activating Q7 (PFET). A high signal is then propagated from battery 301 through transistor Q7 and ultimately to the gate node of transistor Q3, which can cause the connection of battery 301, e.g., as explained earlier.

Figure 4:
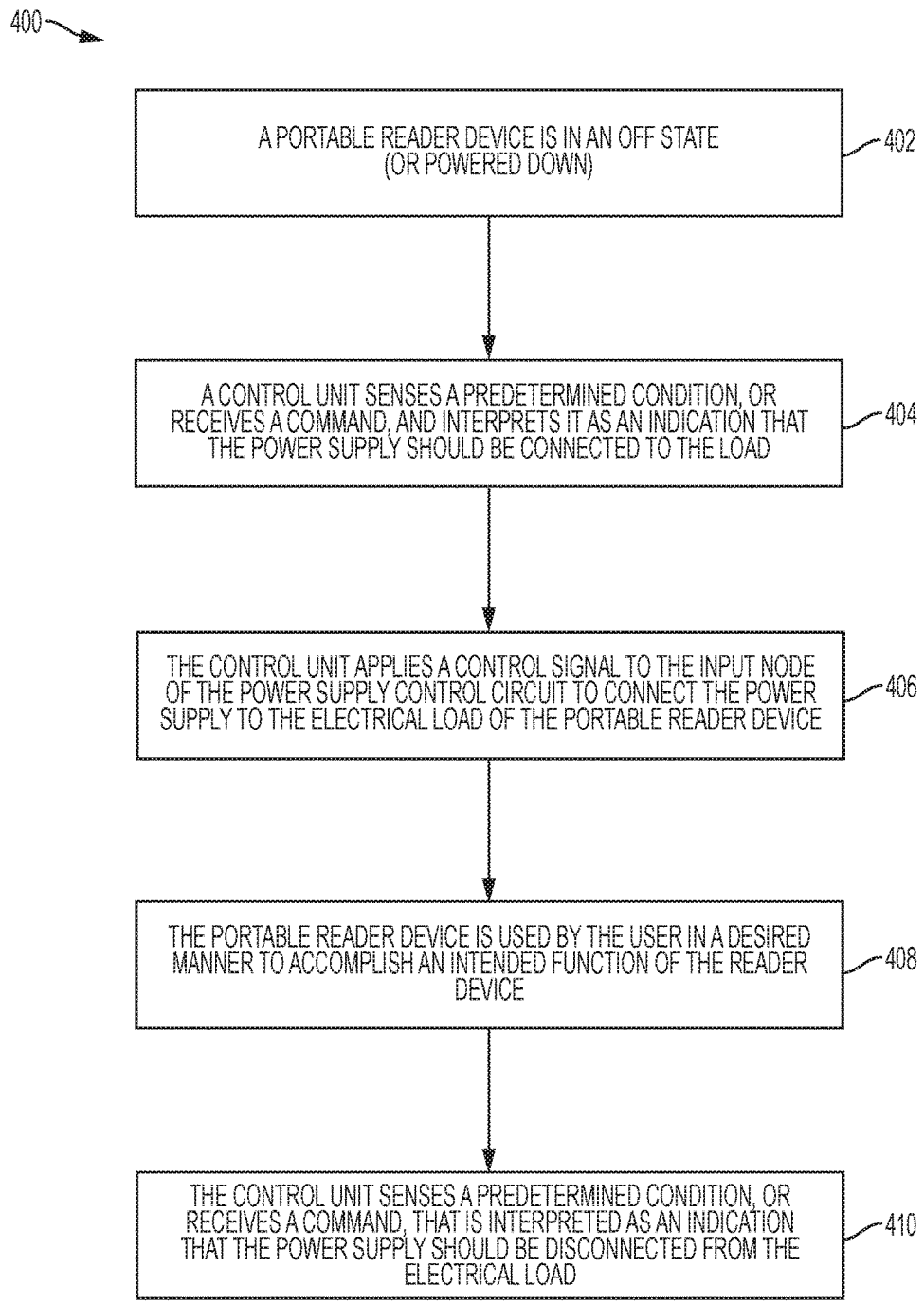
FIG. 4 is a flow diagram depicting example embodiments of methods of operating a display device having a power supply control circuit.

FIG. 4 depicts example embodiments of methods of operating a display device 120 having a control circuit 300 therein, e.g., by connection and/or disconnection of a power supply. Initially, at 402, display device 120 is in an off state (or powered down). This can be prior to a first use or initialization by the user, such as with a dedicated display device prior to being opened from its packaging. At 404, control unit 210 or 260, after being connected to a secondary power source, can sense a predetermined condition, or receive a command, either of which are interpreted as an indication that the power supply (220, 301) should be connected to the electrical load R1 (FIG. 3A). Examples of predetermined conditions and commands are provided above but, for purposes of illustration of this embodiment, the predetermined condition is the recognition of connection to a secondary power source.

Next, at 406, control unit (210, 260) can apply a control signal to input node 310 (or 311) of the power supply control circuit 300 to connect power supply (220, 301) to electrical load R5 of display device 120. The application of the control signal initiates operation of control circuit 300 to transition from the disconnected state to the connected state as described above with respect to FIG. 3. With power supply (220, 301) now being connected, at 408, display device 120 can be used by the user in whatever manner desired. For example, display device 120 can receive a signal from on-body electronics 110 indicative of an analyte level sensed by the in vivo sensor, subsequently process that signal, and then display an analyte level to the user. During this time, power supply (220, 301) remains connected to the electrical load R5, but a very low leakage current is maintained as, for example, no path exhibiting only a resistance exists between the positive terminal of power supply (220, 301) and ground (the only paths pass through a capacitor or one or more transistors, and thus those paths do not exhibit only a resistance and are not subject to higher leakage currents).

At 410, control unit (210, 260) senses a predetermined condition, or receives a command, as described above, that is interpreted as an indication that power supply (220, 301) should be disconnected from the electrical load R1 (FIG. 3). Again, there are many such conditions or commands that can serve as the impetus for disconnection, with one example being a long push of the power button. In response to this, at 412, control unit (210, 260) runs a power down software routine such that display device 120 turns off, but power supply (220, 301) remains connected to the electrical load R5. As described earlier, no electrical path exists between the power supply and a ground node other than through a transistor or a capacitor in control circuit 300, and thus a low leakage can be maintained.

In many instances entities are described herein as being coupled to other entities. It should be understood that the terms "coupled" and "connected" (or any of their forms) are used interchangeably herein. In both cases, these terms are generic to the direct coupling of two entities (without any non-negligible (e.g., parasitic) intervening entities) and the indirect coupling of two entities (with one or more non-negligible intervening entities), as those of ordinary skill in the art will readily recognize that intervening entities can be introduced while still achieving the functions and benefits of the embodiments described herein. Where entities are shown as being directly coupled together, or described as coupled together without the use of the term "directly" or without description of any intervening functional component (other than a conductor), it should be understood that those entities can be indirectly coupled together as well (e.g., with an intervening resistor, capacitor, inductor, transistor, etc.) unless the context clearly dictates otherwise. Likewise, the depiction of two entities that are directly coupled with each other (e.g., with only an intervening conductor and/or node present between the two entities) shall serve as written support for the recitation of those entities being "directly" coupled together in the claims. Likewise, the depiction of two entities that are indirectly coupled with each other (e.g., with an intervening component other than a mere conductor and/or node) shall serve as written support for the recitation of those entities as being "indirectly" coupled together in the claims.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A portable device, comprising:
   a control circuit transitionable from a disconnected state where a power supply is electrically disconnected from an electrical load, to a connected state where the power supply is electrically connected to the electrical load, the control circuit comprising:
   an input node configured to receive a control signal;
   a first transistor activatable to permit the supply of power from the power supply through the first transistor to the electrical load, and deactivatable to prevent the supply of power from the power supply to the electrical load,
   a second transistor coupled with the input node and configured to activate a fourth transistor in response to a first voltage of the control signal; and
   a third transistor coupled with the input node and configured to control the activation of the first transistor in response to a second voltage of the control signal.

2. The portable device of claim 1, wherein no path exhibiting only resistance exists between the power supply and a ground node.

3. The portable device of claim 2, further comprising:
an electrical load adapted to perform a device function; and
a power supply capable of supplying power to the electrical load.

4. The portable device of claim 3, wherein the power supply is contained within a housing of the portable device such that the power supply is not replaceable by a user.

5. The portable device of claim 1, wherein each of the transistors is a field effect transistor (FET), and the first and second transistors are P-type and the third and fourth transistors are N-type.

6. The portable device of claim 5, wherein a source of the first transistor is directly coupled with a source of the second transistor and a positive terminal of the power supply, and wherein a drain of the first transistor is coupled with the electrical load.

7. The portable device of claim 6, wherein a gate of the first transistor is directly coupled with a drain of the third transistor, and wherein a source of the third transistor is coupled with a ground node.

8. The portable device of claim 7, wherein a gate of the second transistor is coupled with the input node and a drain of the fourth transistor, wherein a gate of the fourth transistor is coupled with a drain of the second transistor and a drain of the third transistor, and wherein a source of the fourth transistor is coupled with the ground node.

9. The portable device of claim 8, wherein a resistive feedback is present between the input node and the electrical load.

10. The portable device of claim 9, further comprising:
a first capacitor coupled between a gate of the second transistor and the ground node;
a second capacitor coupled between a positive terminal and a negative terminal of the power supply; and
a third capacitor coupled between a drain of the first transistor and the ground node.

11. The portable device of claim 10, further comprising:
a first resistor coupled between the gate of the second transistor and the drain of the fourth transistor; and
a second resistor coupled between the drain of the second transistor and the gate of the fourth transistor.

12. The portable device of claim 1, wherein every path between a positive terminal of the power supply and a ground node passes through a transistor or a capacitor.

13. The portable device of claim 1, wherein the portable device is a display device configured to receive a signal from an on-body electronics device, the signal being indicative of an analyte level sensed by an in vivo sensor of the on-body electronics device.

14. The portable device of claim 1, wherein the portable device is at least one of: (a) an on-body electronics device configured to sense an analyte level of a subject with an in vivo sensor or (b) an in vitro meter configured to receive a test strip.

15. A method of connecting a power supply to an electrical load in a portable device having a first transistor electrically located between the power supply and the electrical load, a second transistor having a gate coupled to an input node, a third transistor having a gate coupled to the input node, and a fourth transistor, the method comprising:
activating the third transistor with a first voltage applied at the input node;
activating the first transistor with a second voltage applied by the third transistor, wherein activation of the first transistor electrically connects the power supply to the electrical load;
deactivating the fourth transistor with the second voltage; and
deactivating the second transistor, wherein the second transistor is electrically located between the power supply and the fourth transistor.

16. The method of claim 15, wherein the second transistor is deactivated by the first voltage applied at the input node.

17. The method of claim 15, wherein a resistive feedback path is present between the electrical load and the input node, and a first capacitor is coupled between the input node and a ground node, the method further comprising applying an impedance to the input node such that the input node effectively resembles an open circuit.

18. The method of claim 17, wherein the second transistor is deactivated after charging the first capacitor through the resistive feedback path.

19. The method of claim 15, wherein every path between a positive terminal of the power supply and a ground node passes through a transistor or a capacitor.

20. The method of claim 15, wherein no path exhibiting only a resistance exists between a positive terminal of the power supply and a ground node.

* * * * *